(12) United States Patent
Zhou et al.

(10) Patent No.: US 9,150,474 B2
(45) Date of Patent: Oct. 6, 2015

(54) REDUCTION OF ACID WITHIN COLUMN THROUGH ESTERIFICATION DURING THE PRODUCTION OF ALCOHOLS

(75) Inventors: Zhenhua Zhou, Houston, TX (US); Victor J. Johnston, Houston, TX (US); David Lee, Seabrook, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 731 days.

(21) Appl. No.: 13/456,521

(22) Filed: Apr. 26, 2012

(65) Prior Publication Data

US 2012/0238786 A1 Sep. 20, 2012

Related U.S. Application Data

(63) Continuation-in-part of application No. 13/094,488, filed on Apr. 26, 2011, now Pat. No. 8,846,988, and a continuation-in-part of application No. 13/094,641, filed on Apr. 26, 2011, now Pat. No. 8,846,986.

(60) Provisional application No. 61/579,084, filed on Dec. 22, 2011, provisional application No. 61/363,056, filed on Jul. 9, 2010.

(51) Int. Cl.
| | |
|---|---|
| *C07C 29/149* | (2006.01) |
| *C07C 67/08* | (2006.01) |
| *C07C 29/80* | (2006.01) |

(52) U.S. Cl.
CPC .............. *C07C 29/149* (2013.01); *C07C 29/80* (2013.01); *C07C 67/08* (2013.01)

(58) Field of Classification Search
CPC .................................................. C07C 29/149
USPC ........................................................ 568/885
See application file for complete search history.

(56) References Cited

U.S. PATENT DOCUMENTS

| | | | |
|---|---|---|---|
| 1,939,116 A | 12/1933 | Fuchs | |
| 2,649,407 A | 8/1953 | Harrison et al. | |
| 2,702,783 A | 2/1955 | Harrison et al. | |
| 2,744,939 A | 5/1956 | Kennel | |
| 2,859,241 A | 11/1958 | Schnizer | |
| 2,882,244 A | 4/1959 | Milton | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Karl et al. | |
| 3,769,329 A | 10/1973 | Paulik et al. | |
| 3,772,380 A | 11/1973 | Paulik et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,370,491 A | 1/1983 | Bott et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,454,358 A | 6/1984 | Kummer et al. | |
| 4,456,775 A | 6/1984 | Travers et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,569,726 A | 2/1986 | Berg et al. | |
| 4,611,085 A | 9/1986 | Kitson | |
| 4,626,321 A | 12/1986 | Grethlein et al. | |
| 4,628,130 A | 12/1986 | Bournonville et al. | |
| 4,678,543 A | 7/1987 | Houben et al. | |
| 4,692,218 A | 9/1987 | Houben et al. | |
| 4,774,365 A | 9/1988 | Chen et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,047,592 A | 9/1991 | Carpenter | |
| 5,061,671 A | 10/1991 | Kitson et al. | |
| 5,070,016 A | 12/1991 | Hallberg | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,308 A | 2/1993 | Bartley et al. | |
| 5,185,481 A | 2/1993 | Muto et al. | |

(Continued)

FOREIGN PATENT DOCUMENTS

| | | |
|---|---|---|
| CN | 101519349 | 9/2009 |
| EP | 0104197 | 4/1984 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Elvis O Price

(74) *Attorney, Agent, or Firm* — Kilpatrick Townsend & Stockton LLP

(57) ABSTRACT

Purifying and/or recovery of ethanol from a crude ethanol product obtained from the hydrogenation of acetic acid. Separation and purification processes of crude ethanol mixture are employed to allow recovery of ethanol and remove impurities. In addition, the process involves the esterification of acetic acid in a column used for recovering the ethanol.

13 Claims, 3 Drawing Sheets

(56) References Cited

U.S. PATENT DOCUMENTS

| | | |
|---|---|---|
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| 5,527,969 A | 6/1996 | Kaufhold et al. |
| 5,565,068 A | 10/1996 | Parker et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady et al. |
| 5,861,530 A | 1/1999 | Atkins et al. |
| 5,993,610 A | 11/1999 | Berg |
| 5,998,658 A | 12/1999 | Wu et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwoudt et al. |
| 6,444,842 B1 | 9/2002 | Gerberich et al. |
| 6,472,555 B2 | 10/2002 | Choudary et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,755,975 B2 | 6/2004 | Vane et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,091,155 B2 | 8/2006 | Inui et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,594,981 B2 | 9/2009 | Ikeda |
| 7,601,865 B2 | 10/2009 | Verser et al. |
| 7,608,744 B1 | 10/2009 | Johnston et al. |
| 7,652,167 B2 | 1/2010 | Miller et al. |
| 7,667,068 B2 | 2/2010 | Miller et al. |
| 7,682,812 B2 | 3/2010 | Verser et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 2003/0135469 A1 | 7/2003 | Fujita et al. |
| 2004/0152915 A1 | 8/2004 | Fujita et al. |
| 2004/0242917 A1 | 12/2004 | Inui et al. |
| 2005/0197506 A1 | 9/2005 | Scates et al. |
| 2006/0019360 A1 | 1/2006 | Verser et al. |
| 2006/0224013 A1 | 10/2006 | Inui et al. |
| 2006/0252956 A1 | 11/2006 | Miller et al. |
| 2007/0138083 A1 | 6/2007 | Aizawa |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207959 A1 | 8/2008 | Plante et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0130775 A1 | 5/2010 | Voss et al. |
| 2010/0185021 A1 | 7/2010 | Ross et al. |
| 2010/0197485 A1 | 8/2010 | Johnston et al. |
| 2011/0082322 A1 | 4/2011 | Jevtic et al. |
| 2012/0010437 A1 | 1/2012 | Jevtic |
| 2012/0010438 A1 | 1/2012 | Lee et al. |
| 2012/0010439 A1 | 1/2012 | Jevtic |
| 2012/0010440 A1 | 1/2012 | Sarager |
| 2012/0273338 A1 | 11/2012 | Lee et al. |
| 2012/0277481 A1 | 11/2012 | Warner |

FOREIGN PATENT DOCUMENTS

| | | |
|---|---|---|
| EP | 0137749 | 4/1985 |
| EP | 0167300 | 1/1986 |
| EP | 0175558 | 3/1986 |
| EP | 0285420 | 10/1988 |
| EP | 0400904 | 5/1990 |
| EP | 0372847 | 6/1990 |
| EP | 0456647 | 11/1991 |
| EP | 0944572 | 9/1999 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 1-268654 | 10/1989 |
| JP | 4-193304 | 7/1992 |
| JP | 6-116182 | 4/1994 |
| WO | WO 82/03854 | 11/1982 |
| WO | WO 83/03409 | 10/1983 |
| WO | WO 98/25876 | 6/1998 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/055285 | 5/2010 |
| WO | WO 2011/097227 | 8/2011 |
| WO | WO 2011/140460 A2 | 11/2011 |
| WO | WO 2012/006219 | 1/2012 |
| WO | WO 2012/006228 A1 | 1/2012 |

OTHER PUBLICATIONS

ZeaChem, Inc., Technology Overview, Lakewood, Colorado www.zeachem.com, 2008.

Yang et al., Process of Ethanol Synthesis through esterification of acetic acid and economic analysis. No. 4, 2011, 15 Pages.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Perry et al., "Perry's Chemical Engineer's Handbook", 7th Ed. (1997) pp. 22-37 and 22-69.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(56) References Cited

OTHER PUBLICATIONS

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Burkhanov et al., "Palladium-Based Alloy Membranes for Separation of High Purity Hydrogen from Hydrogen-Containing Gas Mixtures", Platinum Metals Rev., 2011, 55, (1), pp. 3-12.

Baker et al., "Membrane separation systems: recent developments and future directions", (1991) pp. 151-169.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Yu Huang et al., "Low-Energy Distillation-Membrane separation Process" Industrial & Engineering Chemistry Research, American Chemical Society, US, vol. 49, No. 8, Jan. 1, 2010, pp. 3760-3768, XP 002657719.

International Search Report and Written Opinion mailed Feb. 23, 2012 in corresponding International Application No. PCT/US2011/042646.

Written Opinion mailed Jul. 9, 2012 in corresponding International Application No. PCT/US2011/042646.

International Search Report and Written Opinion mailed Jul. 11, 2012 in corresponding International Application No. PCT/US2012/035182.

International Search Report and Written Opinion mailed Jul. 11, 2012 in corresponding International Application No. PCT/US2012/035203.

Office Action for corresponding Chinese Appl. No. 201280020217.8 dated Aug. 29, 2014.

Response to Final Office Action for U.S. Appl. No. 13/094,488, filed Oct. 18, 2013.

Response to Final Office Action for U.S. Appl. No. 13/094,661, filed Nov. 25, 2013.

International Preliminary Report on Patentability for PCT/US2012/035182 mailed Nov. 7, 2013.

International Preliminary Report on Patentability mailed Sep. 26, 2012 in corresponding International Application No. PCT/US2011/042646.

International Search Report and Written Opinion mailed Sep. 19, 2012 in corresponding International Application No. PCT/US2011/059882.

Marian Simo et al., "Adsorption/Desorption of Water and Ethanol on 3A Zeolite in Near-Adiabatic Fixed Bed", Industrial & Engineering Chemistry Research, vol. 48, No. 20, Sep. 25, 2009, XP 55027304, pp. 9247-9260.

Tracy J. Benson et al., "Cellulose Based Adsorbent Materials for the Dehydration of Ethanol Using Thermal Swing Adsorption", Adsorption, Kluwer Academic Publishers, BO, vol. 11, No. 1, Jul. 1, 2005, XP 019203738, pp. 697-701.

H. Kita et al., "Synthesis of a Zeolite NaA Membrane for Pervaporation of Water/Organic Liquid Mixtures", Journal of Materials Science Letters, Chapman and Hall Ltd. London, GB, vol. 14, Jan. 1, 1995, XP 001194463, pp. 206-208.

REDUCTION OF ACID WITHIN COLUMN THROUGH ESTERIFICATION DURING THE PRODUCTION OF ALCOHOLS

CROSS REFERENCE TO RELATED APPLICATIONS

This application claims priority to U.S. Provisional App. No. 61/579,084, filed on Dec. 22, 2011. This application is also a continuation-in-part of U.S. application Ser. No. 13/094,488, filed on Apr. 26, 2011, which claims priority to U.S. Provisional App. No. 61/363,056, filed on Jul. 9, 2010. This application is also a continuation-in-part of U.S. application Ser. No. 13/094,641, filed on Apr. 26, 2011, the entire contents and disclosures of which are incorporated herein by reference.

FIELD OF THE INVENTION

The present invention relates generally to production of ethanol and, in particular, to processes for reducing acid within a column. In one embodiment, the acid is reduced through esterification, preferably within a column that is used for recovering ethanol.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step. EP02060555 describes a process for esterifying ethanoic acid and an alcohol to form ethanoates. The ethanoates are hydrogenated to produce ethanol.

The need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, the process comprises the steps of hydrogenating acetic acid from an acetic acid feedstream in a reactor to produce a crude product stream comprising ethanol and acetic acid; reacting acetic acid and ethanol in a reactive distillation column; withdrawing an overhead stream comprising ethyl acetate and a bottom stream comprising ethanol and water; and recovering ethanol from the bottom stream. A catalyst may be used in the reactive distillation column and in some embodiments, the reactive distillation column comprises an acid catalyst. The reactor may comprise a different catalyst than the catalyst in the reactive distillation column. The reactor catalyst may comprise platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron. The liquid stream may comprise less than 40 wt. % acetic acid and the ester enriched stream may comprise less than 10 wt. % acetic acid. The conversion of acetic acid in the reactive distillation column may be greater than 15%, preferably greater than 40%. The total conversion of acetic acid in the reactor and in the distillation column may be greater than 90%. One or more of the non-condensable gases may be removed from the crude product stream prior to reacting with acetic acid and water may be removed from the crude product stream, using an adsorption unit or membrane. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In another embodiment, the process comprises the steps of hydrogenating acetic acid from an acetic acid feedstream in a reactor to produce a crude product stream comprising ethanol and acetic acid, reacting acetic acid and ethanol in a first column, withdrawing a first overhead stream comprising aldehyde and ethyl acetate, and a first bottom stream comprising ethyl acetate, ethanol and water, separating the first bottom stream in a second column to yield a second overhead stream comprising ethanol and ethyl acetate and a second bottom stream comprising water, and separating the second overhead stream in a third column to yield a third overhead stream comprising ethyl acetate and a third bottom stream comprising ethanol.

In another embodiment, the process comprises the steps of providing a crude ethanol product comprising ethanol, water, ethyl acetate, non-condensable gases, and acetic acid; removing one or more non-condensable gases from the crude product to yield a liquid stream; reacting acetic acid and ethanol in the liquid stream in a reactive distillation column to produce an ester enriched stream comprising ethanol, water and ethyl acetate; and recovering ethanol from the ester enriched stream. The ester enriched stream may be further separated into an overhead stream comprising ethyl acetate and a bottom stream comprising ethanol and water. The bottom stream may be dehydrated to recover ethanol and a purified water stream comprising less than 0.5 wt. % acetic acid, preferably less than 0.1 wt. % acetic acid, more preferably less than 0.05 wt. % acetic acid.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
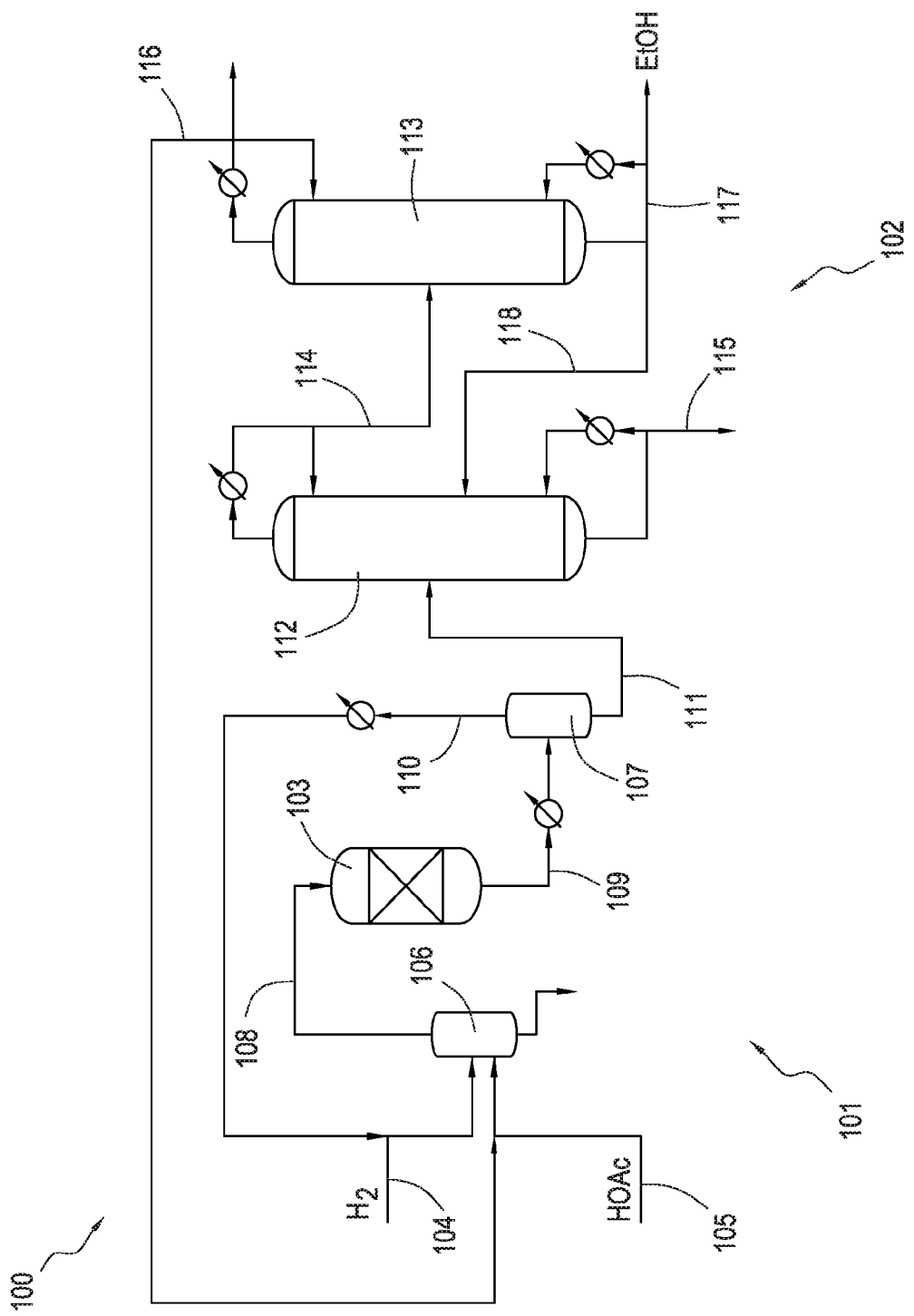
FIG. 1 is a schematic diagram of a reaction system in accordance with one embodiment of the present invention.

The present invention relates to processes for recovering ethanol produced by hydrogenating acetic acid in the presence of a catalyst. The ethanol is recovered from a crude ethanol product comprising a mixture of ethanol, unreacted acetic acid, and optionally ethyl acetate, and impurities such as acetaldehyde and one or more acetals. Water is co-produced with ethanol in the hydrogenation reaction in about a 1:1 molar ratio, and thus producing ethanol also results in the production of water. This makes recovering industrial grade ethanol or fuel grade ethanol difficult due to the excess water. The concentration of unreacted acetic acid in the mixture may vary depending on acetic acid conversion during the hydrogenation reaction. Separating the unreacted acetic acid from the crude reaction mixture requires additional energy. In particular, when acetic acid conversions are high, the crude ethanol product may contain a relatively low amount of acetic acid. Separating this small amount may be disadvantageous and it may be more beneficial to esterify all or a portion of the acetic acid. To improve recovery of ethanol, in one embodiment, the present invention includes a step of esterifying unreacted acetic acid contained in the crude ethanol product to reduce the concentration of the unreacted acetic acid, and thus increase the total conversion of acetic acid. The esterification occurs within the column and may be in the liquid or vapor phase. In this manner, since less acetic acid will be contained in the resulting crude ethanol composition, the energy requirements for ethanol recovery may be advantageously reduced.

The hydrogenation reaction is preferably conducted in the vapor phase, and the crude ethanol product is condensed into a liquid stream (which also may be referred to as a crude ethanol product). In preferred embodiments, light components such as residual hydrogen are removed from the crude ethanol product as a vapor stream. According to the present invention, the liquid stream is esterified in a column, such as a reactive distillation column. The liquid stream once in the column may be esterified in the vapor or liquid phase. In one embodiment, the column may comprise an esterification catalyst, preferably an acid catalyst. In further embodiments, the liquid stream is esterified within a distillation column along with a recycled portion of the recovered ethanol. Although this may reduce the recovery ethanol, it advantageously eliminates the need to separately remove the small amount of acetic acid.

Even at relative high conversions in the hydrogenation reaction, e.g., greater than 90 wt. %, there still may be a significant amount of unreacted acetic acid present in the crude ethanol product. Increasing conversion, although possible, may not reduce the amount of unreacted acid to a desired level. For purposes of the present invention, the term "conversion" refers to the amount of acetic acid in the feed that is converted to a compound other than acetic acid. Conversion is expressed as a percentage based on acetic acid in the feed. Selectivity is expressed as a mole percent based on converted acetic acid. It should be understood that each compound converted from acetic acid has an independent selectivity and that selectivity is independent from conversion. Surprisingly and unexpectedly, esterifying the unreacted acid, along with a minor portion of the ethanol, allows improved recovery of ethanol and reduces overall energy requirements.

Column Esterification of Acetic Acid

FIG. 1 shows a reaction system 100 according to one embodiment of the present invention that comprises a hydrogenation zone 101 and a purification zone 102. The hydrogenation zone 101 comprises a hydrogenation reactor 103, an acetic acid feed line 105 and a hydrogen feed line 104. The purification zone comprises a reactive distillation column 112 and a separation column 113. An acetic acid feedstream 105 comprising acetic acid and hydrogen is directed to hydrogenation reactor 103. Reactor 103 produces a crude ethanol product 109 that is condensed and then separated in flasher 107 into a liquid stream 111 (a liquid crude ethanol product) and a vapor stream 110. Vapor stream 110 may be returned to reactor 103. Liquid stream 111 may comprise unreacted acetic acid depending on the acetic acid conversion.

Preferably the conversion of acetic acid is greater than 60%, e.g., greater than 80%, greater than 90% or greater than 95%. Of course, in order to conduct the desired esterification reaction, some amount of unreacted acetic acid should be present in the crude ethanol product. In one embodiment, liquid stream 111 may comprise less than 40 wt. % unreacted acetic acid, e.g., less than 20 wt. % or less than 10 wt. %. In terms of ranges, liquid stream 111 may comprise from 1 to 40 wt. % unreacted acetic acid, e.g., from 3 to 35 wt. %, or from 5 to 20 wt. %. Lower acetic acid concentrations from 0.01 to 1 wt. % in liquid stream 111 may also be esterified within reactive distillation column 112, depending on economics.

Liquid stream 111 is fed to reactive distillation column 112. In reactive distillation column 112, unreacted acetic acid preferably reacts with ethanol to form ethyl acetate, thus yielding an ester enriched stream 114 comprising ethyl acetate and ethanol. Ethyl acetate in the ester enriched stream 114 may be removed from the reactive distillation column and returned to reactor 103, directly or indirectly, without being further separated from other components. As a result of esterification, the total conversion of acetic acid in reactor 103, may be greater than 90%, e.g., greater than 95% or greater than 99%. As a result of esterification, a water stream in line 115 may be recovered with high purity. In some embodiments, water stream 115 may be separated from ester enriched stream 108 in the residue. Preferably, water stream 115 comprises little, if any, remaining unreacted acetic acid, which may be further neutralized, and/or separated from the water stream 112. In some embodiments, water stream 115 may comprise little, if any acetic acid, e.g., containing less than 5000 wppm acetic acid, less than 1000 wppm acetic acid, and more preferably less than 500 wppm acetic acid.

Embodiments of the present invention reduce unreacted acetic acid concentration without a large penalty to overall ethanol yields. Preferably, the unreacted acetic acid concentration is reduced from liquid stream 111 by at least 15%, e.g., at least 20%, at least 30%, at least 40%, or at least 50%. These reductions, however, are coupled with a minor penalty in ethanol production. Preferably, overall ethanol production is reduced by less than 10%, e.g., less than 5%, or less than 2% relative to the same system but without an esterification unit.

As shown, the ester enriched stream 114 is fed to a light ends column 113 to recover an ethanol product stream 117. The lights stream 116, which may comprise ethyl acetate, may be recycled to reactor 103. Advantageously, in some embodiments of the present invention, improved efficiencies may be realized in recovering ethanol product stream 117 because it is unnecessary to remove residual acetic acid, or, if residual acetic acid is present, less energy is required to remove the residual acetic acid because of its reduced concentration.

In some embodiments where the conversions of acetic acid in the reactive distillation column is low, less than 80%, an optional ethanol feed 118 may be fed to reactive distillation column 112 to react with the remaining acetic acid. Ethanol feed 118 is preferably taken from ethanol product stream 117. In one embodiment, up to 50% of the ethanol from ethanol product stream 117 is recycled as ethanol feed 118, e.g., up to 30%, and more preferably up to 10%. In terms of ranges, from 1 to 50% of the ethanol from ethanol product stream 117 may be recycled as ethanol feed 118, and more preferably from 5 to 10%. The presence of additional ethanol in reactive distillation column 112 may allow an even further reduction of unreacted acetic acid through esterification with ethanol.

In other embodiments, optional ethanol feed 118 may be used with higher conversion of acetic acid in reactor 103, e.g., where conversion is greater than 80%, e.g., greater than 90%, or greater than 95%.

When optional ethanol feed 118 is used, the ester enriched stream 114 may also comprise more ethanol than liquid stream 111. The additional ethanol will vary depending on the amount of ethanol that is fed to reactive distillation column 112 via ethanol feed 118, and ester enriched stream 114 may contain more than 70 wt. % ethanol.

Figure 2:
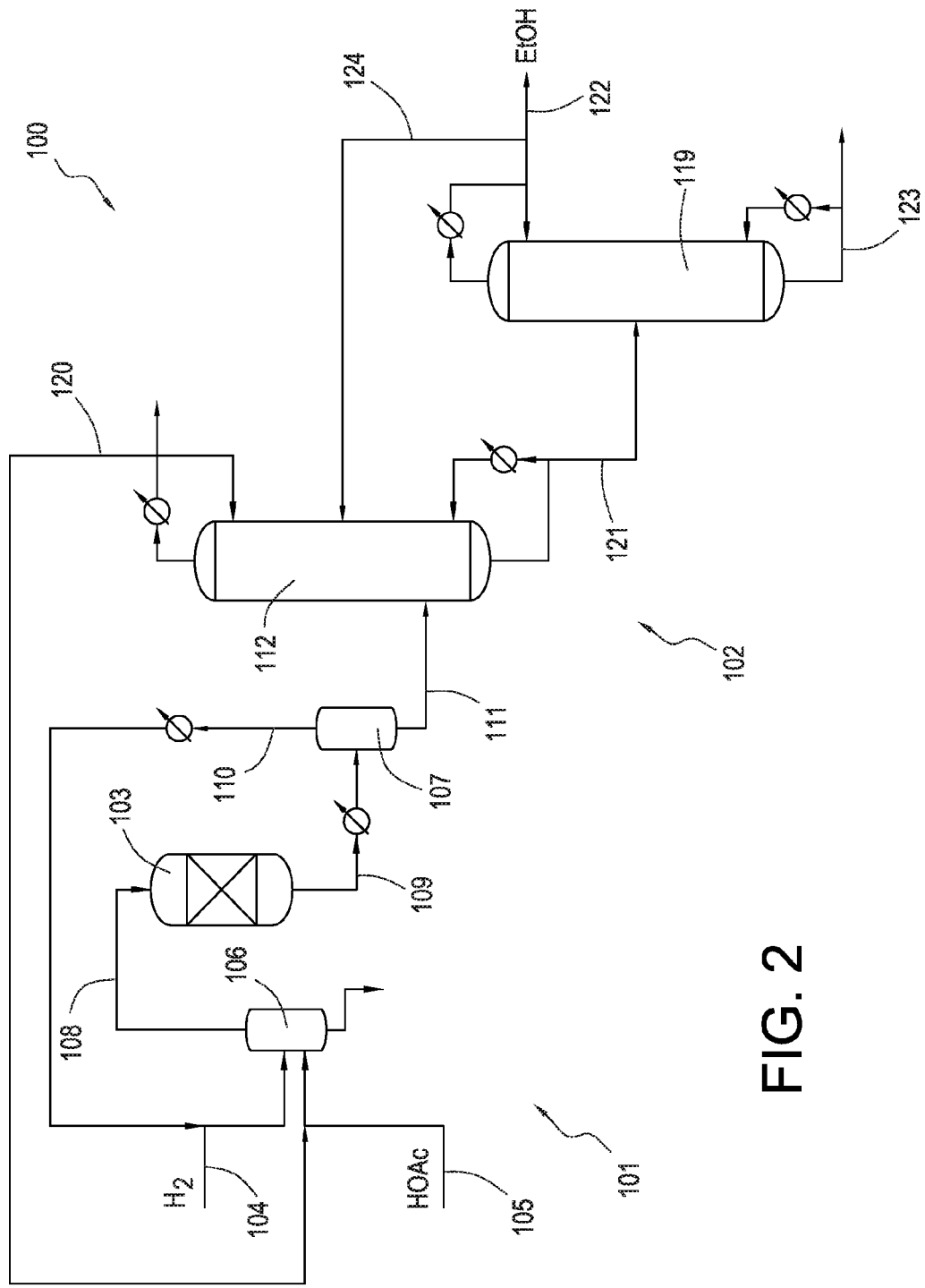
FIG. 2 is a schematic diagram of a reaction system in accordance with one embodiment of the present invention.
Figure 3:
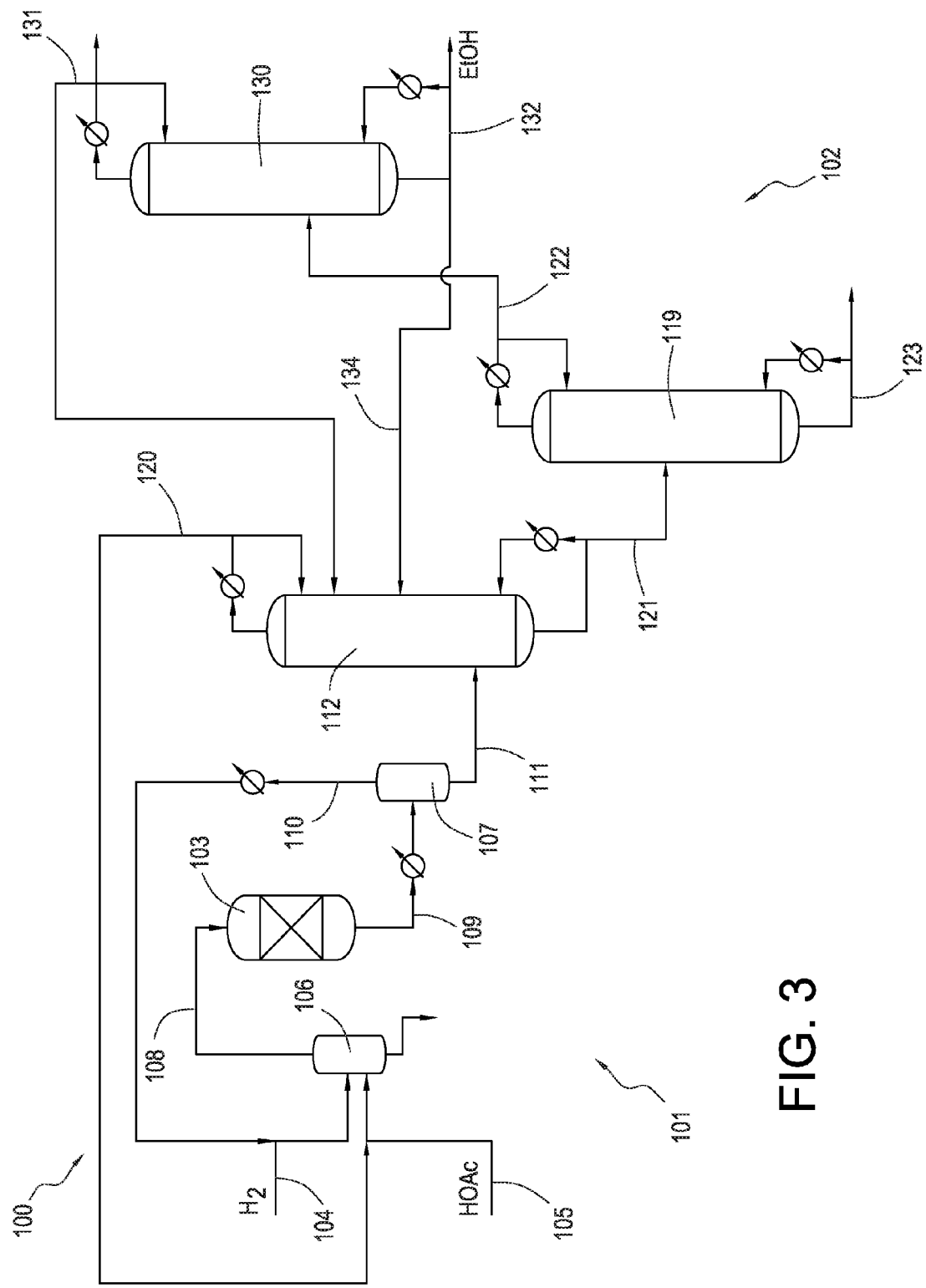
FIG. 3 is a schematic diagram of a reaction system in accordance with one embodiment of the present invention.

FIGS. 2 and 3 show another embodiment in which ethanol is removed from reactive distillation column 112 in the distillate stream 121 with water. The ester enriched stream 120 contains ethyl acetate and a small amount of ethanol. For example, the ester enriched stream 120 comprises less than 30 wt. % ethanol, e.g., less than 20 wt. % or less than 10 wt. %. In terms of ranges, the ester enriches stream 120 comprises from 1 to 30 wt. % ethanol, e.g., from 2 to 20 wt. % ethanol, or from 5 to 10 wt. % ethanol. In an embodiment, the ester enriched stream 120 may be returned to reactor 103 to generate more ethanol.

In another embodiment, ester enriched stream 120 comprises more ethyl acetate than liquid stream 111. As a result of esterification, acetic acid in liquid stream 111 reacts with ethanol to form ethyl acetate, thereby reducing the amount of acetic acid in water stream 123.

As shown, stream 121 is fed to distillation column 119 to yield an overhead stream 122 and a residue stream in line 123. Residue stream 123 may comprise any remaining acetic acid and/or water. In preferred embodiments, it may not be necessary to separate residue stream 123. When separated, residue stream may comprise acetic acid that may be further reacted by esterification, neutralized, and/or separated from the residue stream. Advantageously, as discussed above, in some embodiments of the present invention, improved efficiencies may be realized in recovering ethanol product stream 122 from distillation zone 102, because it is unnecessary to remove residual acetic acid, or, if residual acetic acid is present, less energy is required to remove the residual acetic acid because of its reduced concentration. Therefore, water stream 123 comprises little, if any, acetic acid. For example, water stream 123 may comprise less than 5000 wppm acetic acid, e.g., less than 1000 wppm acetic acid, and more preferably less than 500 wppm acetic acid.

Hydrogenation of Acetic Acid

The process of the present invention may be used with any acetic acid hydrogenation process for producing ethanol. The materials, catalyst, reaction conditions, and separation are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes,* and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola.* Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180 and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syn gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The operating temperatures of the hydrogenation reactor are generally higher than the esterification reactor. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489 and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments, the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. When present, the total weight of the third metal is preferably from 0.05 to 20 wt. %, e.g., from 0.1 to 15 wt. %, or from 0.1 to 7.5 wt. %. In one embodiment, the catalyst may comprise platinum, tin and cobalt.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support, and is present in an amount from 0.1 to 50 wt. %, e.g., from 0.2 to 25 wt. %, from 1 to 20 wt. %, or from 3 to 15 wt. %, based on the total weight of the catalyst. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate mat be crystalline or amorphous.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

The conversion of the hydrogenation reaction may be at least 40%, e.g., at least 50%, at least 60%, at least 70% or at least 80%. Although catalysts that have high conversions are desirable, such as at least 80% or at least 90%, in some embodiments, a low conversion may be acceptable at high selectivity for ethanol. In particular embodiments, low conversion may be used in either reactor when hydrogenation reactors are staged.

Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%. The term "productivity," as used herein, refers to the grams of a specified product, e.g., ethanol, formed during the hydrogenation based on the kilograms of catalyst used per hour. The productivity preferably is from 100 to 3,000 grams of ethanol per kilogram of catalyst per hour.

In various embodiments of the present invention, the crude ethanol product produced by the hydrogenation process, before any subsequent processing, such as purification and separation, will typically comprise unreacted acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0.01 to 90 | 0.5 to 50 | 1 to 35 | 1 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and esterification within reactive distillation column 112 may be justified, depending on economics, for even very low acetic acid concentration, such as from 0.01 to 1 wt. %. However, it is preferred that the crude ethanol product comprises from 1 to 40 wt. % unreacted acetic acid, e.g., from 3 to 35 wt. %, or from 5 to 20 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

An exemplary hydrogenation system 100 is shown in FIGS. 1, 2 and 3 and is described in further detail below. System 100 comprises reaction zone 101 and distillation zone 102. In reaction zone 101, hydrogen and acetic acid are fed to a vaporizer 106 via lines 104 and 105 respectively, to create a vapor feed stream in line 108 that is directed to hydrogenation reactor 103. Hydrogen feed line 105 may be preheated to a temperature from 30° C. to 150° C., e.g., from 50° C. to 125° C. or from 60° C. to 115° C. Hydrogen feed line 105 may be fed at a pressure from 1300 kPa to 3100 kPa, e.g., from 1500 kPa to 2800 kPa, or 1700 kPa to 2600 kPa. In one embodiment, lines 104 and 105 may be combined and jointly fed to the vaporizer 106. The temperature of the vapor feed stream in line 108 is preferably from 100° C. to 350° C., e.g., from 120° C. to 310° C. or from 150° C. to 300° C. Any feed that is not vaporized is removed from vaporizer 106, as shown in FIGS. 1, 2 and 3, and may be recycled or discarded thereto. In addition, although FIGS. 1, 2 and 3 show line 108 being directed to the top of reactor 103, line 108 may be directed to the side, upper portion, or bottom of reactor 103. Further modifications and additional components to reaction zone 102 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In certain embodiments of the invention, the guard bed media is functionalized to trap particular species such as sulfur or halogens. During the hydrogenation process, a crude ethanol product is withdrawn, preferably continuously, from reactor 103 via line 109.

Crude ethanol product 109 may be condensed and fed to flasher 107, which, in turn, provides a vapor stream and a liquid stream. The flasher 107 may operate at a temperature of from 50° C. to 250° C., e.g., from 30° C. to 225° C. or from 60° C. to 200° C. The pressure of flasher 210 may be from 50 kPa to 2500 kPa, e.g., from 75 kPa to 2250 kPa or from 100 to 2100 kPa.

The vapor stream exiting the flasher 107 may comprise hydrogen, hydrocarbons, and other non-condensable gases, which may be purged and/or returned to reaction zone 101 via line 110.

Optionally, crude ethanol product 109 may pass through one or more membranes to separate hydrogen and/or other non-condensable gases.

The liquid in line 111 from flasher 107 is fed to a reactive distillation column 112 where unreacted acetic acid may be esterified with ethanol to form ethyl acetate. Reactive distillation column. Reactive distillation column 112 produces a distillate in line 114 comprising ethanol, ethyl acetate and acetaldehyde, and a water residue in line 115. In one embodiment, column 112 is a tray column having from 5 to 70 trays, e.g., from 15 to 50 trays or from 20 to 45 trays.

In some embodiments, reactive distillation column 112 may comprise a reaction zone that contains a catalyst, such as an acidic catalyst. Suitable catalysts include, without limitation, alkyl sulfonic acids and aromatic sulfonic acids, e.g., methane sulfonic acid, benzene sulfonic acid and p-toluene sulfonic acid. Alternatively, sulfuric acid or heteropoly acids can be used within the scope of the invention. A variety of homogeneous or heterogeneous acids may also be employed within the scope of this invention.

The present invention allows for improved recovery of ethanol using less energy because acetic acid is removed in the distillate as ethyl acetate. Acetic acid in the crude product is preferably consumed in reactive distillation column 112, e.g., at least 15%, at least 30%, at least 40%, or at least 50% of the acetic acid is consumed. In reacting the acetic acid, a portion of the ethanol is also consumed. Preferably less than 25% of the ethanol in the crude product is consumed, and more preferably less than 5%. The residue in line 115 may comprise any remaining amounts of acetic acid, but preferably is substantially free of acetic acid, e.g., containing less than 5000 wppm acetic acid, and more preferably less than 500 wppm acetic acid. Optionally, residue in line 115 may be neutralized to remove residual acetic acid. The reaction may produce additional amounts of ethyl acetate and/or water than is present in the crude ethanol product. A majority of the ethyl acetate preferably is withdrawn from column 112 in the distillate in line 114 with the ethanol and the water is withdrawn in the residue in line 115.

As shown in FIG. 1, in column 112, water, any unreacted acetic acid and other heavy components, if present, are removed from the crude product and are withdrawn, preferably continuously, as residue in line 115. In some embodiments, it may be preferable to withdraw a majority of the water in the residue. Reactive distillation column 112 also forms an overhead distillate, which is withdrawn in line 114, and which may be condensed and refluxed, for example, at a ratio of from 10:1 to 1:10, e.g., from 3:1 to 1:3 or from 1:2 to 2:1.

When column 112 is operated under 170 kPa pressure, the temperature of the residue exiting in line 115 preferably is from 120° C. to 150° C., e.g., from 128° C. to 142° C. or from 136° C. to 143° C. The temperature of the distillate exiting in line 114 preferably is from 85° C. to 95° C., e.g., from 85° C. to 91° C. or from 87° C. to 95° C. In some embodiments, the pressure of the reactive distillation column 112 may range from 0.1 kPa to 510 kPa, e.g., from 1 kPa to 475 kPa or from 1 kPa to 375 kPa. Exemplary components for the distillate and residue compositions for the column 112 are provided in Table 2, below. It should be understood that the distillate and residue may also contain other components, not listed in Table 2.

TABLE 2

REACTIVE DISTILLATION COLUMN 112 (FIG. 1)

|  | Conc. (wt. %) | Conc. (wt. %) | Conc. (wt. %) |
|---|---|---|---|
| First Distillate |  |  |  |
| Ethyl Acetate | <55 | 1 to 50 | 3 to 45 |
| Acetaldehyde | <10 | 0.1 to 5 | 0.3 to 3 |
| Water | <15 | 0.1 to 10 | 0.3 to 7 |
| Ethanol | 35 to 100 | 40 to 98 | 45 to 96 |
| Acetal | <10 | 0.1 to 5 | 0.2 to 3 |
| First Residue |  |  |  |
| Water | 15 to 100 | 40 to 95 | 50 to 90 |
| Ethanol | 0.01 to 40 | 0.1 to 25 | 0.1 to 20 |
| Ethyl Acetate | <2 | 0.001 to 1 | 0.01 to 0.5 |
| Acetic Acid | 0.01 to 50 | 0.1 to 30 | 0.1 to 10 |

Some species, such as acetals, may decompose in column 112 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This equilibrium may be regulated using the residence time and/or temperature of crude ethanol product.

As shown in FIG. 1, the distillate in line 114, which comprises ethanol, ethyl acetate and/or acetaldehyde, preferably is refluxed as shown, for example, at a reflux ratio of from 1:30 to 30:1, e.g., from 1:5 to 5:1 or from 1:3 to 3:1. First distillate in line 114 is introduced to the second column 113 preferably in the top part of column, e.g., top half or top third. Column 113 may be a tray column or packed column. In one embodiment, column 113 is a tray column having from 5 to 70 trays, e.g., from 15 to 50 trays or from 20 to 45 trays.

Optionally, the light ends column may be an extractive distillation column. Suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may be an aqueous stream comprising water. If the extraction agent comprises water, the water may be obtained from an external source or from an internal return/recycle line from one or more of the other columns, such as from a portion of the water stream 115. Generally, the extractive agent is fed above the entry point of distillate in line 114. When extractive agents are used, a suitable recovery system, such as a further distillation column, may be used to remove the extractive agent and recycle the extractive agent.

In one aspect the distillate in line 116 or a portion thereof, may be returned to reactor 103. In some embodiments, it may be advantageous to return a portion of distillate to reactor 103. The ethyl acetate and/or acetaldehyde in the distillate may be further reacted in hydrogenation reactor 103 or in a secondary reactor. The outflow from the secondary reactor may be fed to reactor 103 to produce additional ethanol or to a distillation column to recover additional ethanol.

Depending on the amount of water and acetic acid contained in the residue of column 113, line 117 may be treated in one or more of the following processes. The following are exemplary processes for further treating first residue and it should be understood that any of the following may be used regardless of acetic acid concentration. Although most of the acetic acid should be esterified, any remaining acetic acid may be separated from the water. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where residue in line 115 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility.

In an optional embodiment, depending on the amount of acetic acid in column 112, a derivative ethanol stream in line 118 may be returned to the reactive distillation column to react with any remaining acetic acid in column 112. For example, optionally, less than 10% of the ethanol in the second residue is returned to the reactive distillation column 112. In one embodiment, derivative ethanol stream in line 118 is directed to a feed point below the feed point of crude ethanol product in line 111.

Residue in line 117 may contain water. Depending on the desired ethanol product, it may be desired to further dry the residue in line 117. Residual water removal may be accomplished, for example, using one or more adsorption units, membranes, molecular sieves, extractive distillation, or a combination thereof. Suitable adsorption units include pressure swing adsorption units and thermal swing adsorption units.

Optionally, crude ethanol product in line 111 may be further fed to an esterification reactor, hydrolysis reactor, hydrogenolysis reactor, or combination thereof. An esterification reactor may be used to consume acetic acid present in the crude ethanol product to further reduce the amount of acetic acid that would otherwise need to be removed. Hydrolysis may be used to convert ethyl acetate into acetic acid (which may be recycled to reaction zone 101) and ethanol, while hydrogenolysis may be used to convert ethyl acetate in the crude ethanol product to ethanol.

FIG. 2 shows a different embodiment where the ethanol is removed from a low temperature reactive distillation column in the residue. The crude ethanol product in line 111 is fed to reactive distillation column 112 to yield a distillate in line 120 comprising ethanol and acetaldehyde and a residue comprising water and ethanol.

A majority of the acetic acid in the crude product is preferably consumed in reactive distillation column. Therefore, the first distillate is substantially free of acetic acid, less than 5000 wppm acetic acid, and more preferably less than 500 wppm acetic acid. In an embodiment, a majority of the ethyl acetate preferably is withdrawn from column 112 in the distillate in line 120 with acetaldehyde and ethanol and water is withdrawn in the residue in line 121.

The reactive distillation column in this embodiment operates under different perimeters such that ethanol is removed in the residue with water. When column 112 is operated under 170 kPa pressure, the temperature of the residue exiting in line 121 preferably is from 120° C. to 150° C., e.g., from 128° C. to 142° C. or from 136° C. to 143° C. The temperature of the distillate exiting in line 120 preferably is from 85° C. to 95° C., e.g., from 85° C. to 91° C. or from 87° C. to 95° C. In some embodiments, the pressure of the reactive distillation column 112 may range from 0.1 kPa to 510 kPa, e.g., from 1 kPa to 475 kPa or from 1 kPa to 375 kPa. Exemplary components for the distillate and residue compositions for the column 112 are provided in Table 3, below. It should be understood that the distillate and residue may also contain other components, not listed in Table 3.

TABLE 3

REACTIVE DISTILLATION COLUMN 112 (FIG. 2)

|  | Conc. (wt. %) | Conc. (wt. %) | Conc. (wt. %) |
| --- | --- | --- | --- |
| First Distillate |  |  |  |
| Ethyl Acetate | <55 | 1 to 50 | 3 to 45 |
| Acetaldehyde | <10 | 0.1 to 5 | 0.3 to 3 |
| Water | <15 | 0.1 to 10 | 0.3 to 7 |
| Ethanol | <40 | 0.01 to 30 | 0.01 to 25 |
| Acetal | <10 | 0.1 to 5 | 0.2 to 3 |
| First Residue |  |  |  |
| Water | <40 | 0.001 to 30 | 0.001 to 25 |
| Ethanol | 35 to 100 | 40 to 98 | 45 to 96 |
| Ethyl Acetate | <2 | 0.001 to 1 | 0.01 to 0.5 |
| Acetic Acid | <10.0 | <5.0 | <1.0 |

As shown in FIG. 2, the distillate in line 120, which comprises ethyl acetate and/or acetaldehyde, preferably is refluxed as shown, for example, at a reflux ratio of from 1:30 to 30:1, e.g., from 1:5 to 5:1 or from 1:3 to 3:1. First residue is fed via line 121 to second column 119, also referred to as a "product column." The first residue in line 119 is introduced in the lower part of second column 119, e.g., lower half or lower third. Second column 119 recovers ethanol as the distillate in line 122. The distillate of second column 122 preferably is refluxed as shown in FIG. 2, for example, at a reflux ratio of from 1:10 to 10:1, e.g., from 1:3 to 3:1 or from 1:2 to 2:1. Second column 119 is preferably a tray column as described above and preferably operates at atmospheric pressure. The temperature of the second distillate exiting in line 122 from second column 119 preferably is from 60° C. to 110° C., e.g., from 70° C. to 100° C. or from 75° C. to 95° C. The temperature of the second residue 123 exiting from second column 119 preferably is from 70° C. to 115° C., e.g., from 80° C. to 110° C. or from 85° C. to 105° C., when the column is operated at atmospheric pressure. Exemplary components of the distillate and residue compositions for second column 119 are provided in Table 4 below. It should be understood that the distillate and residue may also contain other components, not listed, such as components in the feed.

TABLE 4

SECOND COLUMN 119 (FIG. 2)

|  | Conc. (wt. %) | Conc. (wt. %) | Conc. (wt. %) |
| --- | --- | --- | --- |
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <15 | 0.001 to 10 | 0.005 to 2 |

Any of the compounds that are carried through the distillation process from the feed or crude reaction product generally remain in the second distillate in amounts of less 0.1 wt. %, based on the total weight of the second distillate composition, e.g., less than 0.05 wt. % or less than 0.02 wt. %.

In one embodiment, as shown in FIG. 3, the second distillate in line 122 is fed to a third column 130, e.g., ethanol product column, for separating the second distillate into a third distillate (ethyl acetate distillate) in line 131 and a third residue (ethanol residue) in line 132. Second distillate in line 122 may be introduced into the lower part of column 130, e.g., lower half or lower third. Third distillate 131 is preferably refluxed, for example, at a reflux ratio greater than 2:1, e.g., greater than 5:1 or greater than 10:1. At least a portion of third distillate 131 may be returned to hydrogenation zone 101 and/or purged as necessary. As shown in FIG. 3, third distillate in line 131 is fed to upper portion of first column 112 and may then be returned to hydrogenation zone 101. Third column 130 is preferably a tray column as described herein and preferably operates at atmospheric pressure. The temperature of the third residue exiting from third column 130 preferably is from 60° C. to 110° C., e.g., from 70° C. to 100° C. or from 75° C. to 95° C. The temperature of the third distillate exiting from third column 130 preferably is from 70° C. to 115° C., e.g., from 80° C. to 110° C. or from 85° C. to 105° C., when the column is operated at atmospheric pressure.

In one embodiment, a portion of third residue in line 132 is returned to first column 112 to esterify the acetic acid via line 134. The returned ethanol in line 134 may be fed above the feed point of liquid stream 111. Preferably less than 50% of the third residue in line 132 is used to esterify the acetic acid in first column 112, e.g., less than 30% or less than 10%.

The remaining water from the second distillate in line 122 may be removed in further embodiments of the present invention. Depending on the water concentration, the ethanol product may be derived from the second distillate in line 122 as shown in FIG. 2 or the third residue in line 132 as shown in FIG. 3. Some applications, such as industrial ethanol applications, may tolerate water in the ethanol product, while other applications, such as fuel applications, may require an anhydrous ethanol. The amount of water in the distillate of line 122 or the residue of line 132 may be closer to the azeotropic amount of water, e.g., at least 4 wt. %, preferably less than 20 wt. %, e.g., less than 12 wt. % or less than 7.5 wt. %. Water may be removed from the second distillate in line 122 or the third residue in line 132 using several different separation techniques as described herein. Particularly preferred techniques include the use of distillation column, membranes, adsorption units, and combinations thereof. The ethanol product is separated using the columns as described above and may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications.

The ethanol product may be an industrial grade ethanol or fuel grade ethanol. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 85 to 99.9 | 90 to 99.5 | 92 to 99.5 |
| Water | <12 | 0.1 to 9 | 0.5 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene.

The associated condensers and liquid separation vessels that may be employed with each of the distillation columns may be of any conventional design and are simplified in FIGS. 1, 2 and 3. As shown in FIGS. 1, 2 and 3, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIGS. 1, 2 and 3, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol comprising:
hydrogenating acetic acid from an acetic acid feedstream in a reactor to produce a crude product stream comprising ethanol and acetic acid;
reacting acetic acid and ethanol in a reactive distillation column;
withdrawing an overhead stream comprising ethyl acetate and a bottom stream comprising ethanol and water; and
recovering ethanol from the bottom stream.

2. The process of claim 1, wherein a catalyst is used in the reactive distillation column.

3. The process of claim 1, wherein the reactor comprises a different catalyst than the reactive distillation column.

4. The process of claim 1, wherein the reactive distillation column comprises an acid catalyst.

5. The process of claim 1, wherein the liquid stream comprises less than 40 wt. % acetic acid.

6. The process of claim 1, wherein the ester enriched stream comprises less than 10 wt. % acetic acid.

7. The process of claim 1, wherein the conversion of acetic acid in the reactive distillation column is greater than 15%.

8. The process of claim 1, wherein the conversion of acetic acid in the reactive distillation column is greater than 40%.

9. The process of claim 1, wherein the total conversion of acetic acid in the first reactor and the reactive distillation column is greater than 90%.

10. The process of claim 1, further comprising removing one or more non-condensable gases from the crude product stream prior to reacting with acetic acid.

11. The process of claim 1, further comprising removing water from the crude product stream using an adsorption unit or a membrane.

12. The process of claim 1, wherein the first reactor comprises a hydrogenation catalyst selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron.

13. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

\* \* \* \* \*